United States Patent
Wijnberg et al.

(10) Patent No.: US 6,639,103 B1
(45) Date of Patent: Oct. 28, 2003

(54) 3-OXOPROPANE-1-SULPHONIC ACIDS AND SULPHONATES

(75) Inventors: Hans Wijnberg, Groningen (NL); Kees Pouwer, Groningen (NL); Jose Nieuwenhuijzen, Groningen (NL); Ton Rene Vries, Groningen (NL)

(73) Assignee: DSM N.V. (NL)

( * ) Notice: Subject to any disclaimer, the term of this patent is extended or adjusted under 35 U.S.C. 154(b) by 0 days.

(21) Appl. No.: 10/069,167

(22) PCT Filed: Aug. 18, 2000

(86) PCT No.: PCT/NL00/00577

§ 371 (c)(1),
(2), (4) Date: Jul. 16, 2002

(87) PCT Pub. No.: WO01/14327

PCT Pub. Date: Mar. 1, 2001

(30) Foreign Application Priority Data

Aug. 19, 1999 (NL) .............................................. 1012865

(51) Int. Cl.[7] ...................... C07C 309/00; C07C 309/01
(52) U.S. Cl. ........................................... 562/46; 562/45
(58) Field of Search ............................. 562/30, 41, 42, 562/45, 46

(56) References Cited

U.S. PATENT DOCUMENTS 2,455,282 A * 11/1948 Thurston ...................... 521/39
6,235,927 B1 * 5/2001 Vries et al. .................. 562/401

OTHER PUBLICATIONS

CA:77:90297 abs of Pulp Pap. Mag. Can. by Meshitsuka et al 73(6) pp T165–T168 1972.*

CA:114:41714 abs of Chemiczne by Rachwal S 32 pp 93–104 1989.*

CA:93:114288 abs of Helvetica Chimica Acta by Pfoertner Karl 63(3) , pp 664–7 1980.*

* cited by examiner

Primary Examiner—Jean F. Vollano
(74) Attorney, Agent, or Firm—Morrison & Foerster LLP

(57) ABSTRACT

The invention relates to 1,3-disubstituted-3-oxopropane-1-sulfonic acids and sulfonates and enantiomerically inriched forms thereof. The invention further relates to the use of these enantiomerically inriched compounds to resolve mixtures of enantiomers, in particular mixtures of enantiomers of amino-functionalized compounds.

15 Claims, No Drawings

3-OXOPROPANE-1-SULPHONIC ACIDS AND SULPHONATES

This is the national stage of PCT/NL 00/00577 filed Aug. 18, 2000, now WO 01/14327.

The present invention relates to 3-oxopropane-1-sulphonic acids and sulphonates, optionally in enantiomerically enriched form. The invention further relates to the use or enantiomerically enriched 3-oxopropane-1-sulphonic acids and sulphonates in the resolution or mixtures or enantiomers, for instance racemic mixtures. The invention relates in particular to (d)- and (l)-enantiomers of 3-oxopropane-1-sulphonic acids of general formula I or a salt thereof:

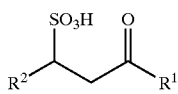

wherein $R^1$ and $R^2$ each independently represent a (cyclo)alkyl, an aryl, an aralkyl or an alkaryl group, wherein the groups optionally contain one or more heteroatoms, for instance O, S or N or wherein $R^1$ and $R^2$ together with the C-atoms to which they are attached and the intermediate C-atom form a 5–8 membered ring which may contain one or more, for instance 1–4, preferably 1–2 heteroatoms, with an ee >80%, preferably >90%, in particular >95%. The invention relates more in particular to 1,3-diphenyl-3-oxopropane-1-sulphonic acids of general formula I or a salt thereof, in particular the (d)- and (l)-enantiomers of these compounds, wherein $R^1$ and/or $R^2$ represent a phenylgroup, optionally substituted with one or more, in particular 1–5, groups $R^3$, wherein the groups $R^3$ each independently represent H, halogen, hydroxy, a (cyclo)alkyl, aryl, alkaryl, aralkyl, (cyclo)alkoxy, aryloxy, amido, amino, nitro, acyl, carboxyl, aryloxycarbonyl, thiol or thioether group. Preferably $R^1$ and $R^2$ both represent an optionally substituted phenyl group.

It is known that sulphonic acids are strong acids and that such compounds could facilitate complex formation, in particular salt formation, in the resolution of mixtures of enantiomers (i.e. racemic mixtures or mixtures with a certain enantiomeric excess). A number of enantiomerically enriched sulphonic acids are known to be useful resolving agents, for instance camphor sulphonic acid (K. J. Brown, M. S. Berry, J. R. Murdoch, J. Org. Chem. 50, 4345, 1985; R. Dumont, A. Brossi, J. V. Silverton, J. Org. Chem. 51, 2515, 1986) and phenylethane sulphonic acid (R. Yoshioka, O. Ohtsuki, M. Senuma, T. Tosa, Chem. Pharm. Bull. 37, 883, 1989; E. J. Corey, K. A. Cimprich, Tetrahedron Lett. 33, 4099, 1992; R. Yoshioka, M. Tohyama, O. Ohtsuki, S. Yamada, I. Chibata, Bull. Chem. Soc. Jpn. 60, 649, 1987; R. Yoshioka, O. Ohtsuki, T. Da-Te, K. Okamura, M. Senuma, Bull. Chem. Soc. Jpn. 67, 3012, 1994). In Tetrahedron Lett. 33, 4099, 1992 Nobel prize winner Prof. E. J. Corey reports that chiral sulphonic acids are difficult to prepare. Chiral sulphonic acids would be very suitable in particular for the resolution of racemic mixtures of amines and amino acids (R. Yoshioka, O. Ohtsuki, T. Da-Te, K. Okamura, M. Senuma, Bull. Chem. Soc. Jpn. 67, 3012, 1994).

The present invention now provides resolving agents, which can be easily prepared and, therefore, are readily accessible.

Examples of 1,3-disubstituted-3-oxopropane-1-sulphonic acids and sulphonates (these derivatives are derived from the α,β-unsaturated carbonyl compounds of the type 1,3-disubstituted-2-propene-1-one; the 1,3-diphenyl-2-propene-1-one derivatives are known as "chalcones") or related compounds are known in the literature.

1,3-disubstituted-3-oxopropane-1-sulphonic acids and sulphonates and more particularly 1,3-diaryl-3-oxopropane-1-sulphonic acids and sulphonates, can be prepared by addition of sodium bisulphite to the C=C bond of the corresponding α,β-unsaturated ketones (E. Knoevenagel, Ber. 31, 4038, 1904; K. H. Pfoertner, Helv. Chim. Acta 63, 664, 1980) according to the general reaction equations:

where $MHSO_3$ stands for, for instance, sodium or potassium bisulphite.

In the literature the applicant has found the following compounds:
3-(2-hydroxyphenyl)-1-(4-hydroxy-3-methoxyphenyl)-3-oxopropane-1-sulphonic acid (a),
1-(3,4-dimethoxyphenyl)-3-(4-hydroxy-3-methoxyphenyl)-3-oxopropane-1-sulphonic acid (b),
1-(3,4-dimethoxyphenyl)-3-(2-hydroxy-3-methoxy)-3-oxopropane-1-sulphonic acid (c),
barium 1-(3,4-dimethoxyphenyl)-3-(2-hydroxy-3-methoxy)-3-oxopropane-1-sulphonate (d),
1-phenyl-3-(2-hydroxyphenyl)-3-oxopropane-1-sulphonic acid (e),
sodium 1-phenyl-3-(2-hydroxyphenyl)-3-oxopropane-1-sulphonate (f),
1-phenyl-3-(2-hydroxy-3-methoxy-5-methylphenyl)-3-oxopropane-1-sulphonic acid (g),
sodium 1-phenyl-3-(2-hydroxy-3-methoxy-5-methylphenyl)-3-oxopropane-1-sulphonate (h)
1-phenyl-3-(4-hydroxy-3-methoxyphenyl)-3-oxopropane-1-sulphonic acid (i),
sodium 1-phenyl-3-(4-hydroxy-3-methoxyphenyl)-3-oxopropane-1-sulphonate (j),
sodium 1,3-diphenyl-3-oxopropane-1-sulphonate (k),
sodium 3-(p-chlorophenyl)-1-(2-pyridyl)-3-oxopropane-1-sulphonate (1),.
sodium 3-(p-chlorophenyl)-1-(3-pyridyl)-3-oxopropane-1-sulphonate (m).
sodium 3-(p-chlorophenyl)-1-(4-pyridyl)-3-oxopropane-1-sulphonate (n), and
sodium 3-(p-methoxyphenyl)-1-(4-pyridyl)-3-oxopropane-1-sulphonate (o).

Compounds (a) and (b) are described in O. Dahlman, K. Maanson, J. Wood Chem Technol. 16, 47, 1996 ("Analysis of low molecular weight lignin-derived sulphonates by capillary zone electrophoresis"). Compounds (c) and (d) are described in H. Richtzenhuin, B. Afredsson, Ber. 89, 378, 1956. Compounds (e) and (f) are described in H. Richtzenhuin, Ber. 72, 2152, 1939, and in K. Kratzl, H. D äubner, Monatsh. Chem. 78, 376, 1948. Compounds (g) and (h) are described in M. F. Browne, R. L. Shriner, J. Org. Chem. 22, 1320, 1957. Compounds (i) and (j) are described by K. Kratzl, H. Daubner, in Ber. 77, 519, 1944 and Ber. 79, 895, 1946. Compounds (k)–(o) are described in K. H. Pfoertner, Helv. Chim. Acta 63, 664, 1980 ("Substituted alkyl sulphonates by addition of sodium hydrogensulphite to chalcones"). Organic salts of such sulphonic acids are described by S. Rachwal, Zesz. Nauk. Uniw. Jagiellon, Pr. Chem. 32, 93, 1989 ("Addition of amine hydrosulphites to vinyl ketones. Conformation of the gamma-oxoalkanesulphonate anions"). However, in the abovementioned literature sources only the chemical composition of the compounds is disclosed without any suggestion of chirality or enantiomerical enrichment.

The present invention therefore relates to a (d)- or (l)-enantiomer of a sulphonic acid of general formula I or a salt thereof wherein $R^1$ and $R^2$ are as defined above.

Suitable examples of $R^1$ and $R^2$ are, for instance, a $C_1$–$C_8$ alkyl or a $C_3$–$C_{12}$ cycloalkyl group, a 6-ring aryl group, a $C_7$–$C_{12}$ alkaryl group, a $C_7$–$C_{12}$ arylalkyl group, a $C_4$ or a $C_5$ heterocycloalkyl or $C_4$ or $C_5$ heteroaryl group, a $C_5$–$C_{12}$ heterocycloalkyl or $C_5$–$C_{12}$ heteroarylalkyl group or a $C_5$–$C_{12}$ alkylheterocycloalkyl or $C_5$–$C_{12}$ alkylheteroaryl group, in particular methyl, ethyl, n- and i-propyl, n-, s- and t-butyl, pentyl, hexyl, cyclopropyl, cyclobutyl, cyclopentyl, cyclohexyl, phenyl, 1-naphthyl, o-, m- and p-methylphenyl, 2,4,6-trimethylphenyl, p-(t-butyl)phenyl, phenylmethyl, 2-phenylethyl, N-, O-and/or S-containing, unsaturated or saturated rings, in particular five or six rings for instance thienyl, furyl, pyranyl, pyrrolyl, imidazolyl, pyrazolyl, pyridyl, pyrazinyl, pyrimidinyl, pyridazinyl, isothiazolyl, pyrrolidinyl, pyrrolinyl, isoxazolyl, imidazolidinyl, imidazolinyl, pyrazolidinyl, pyrazolinyl, piperidyl and piperazinyl.

Preferably $R^1$ and/or $R^2$ represent a substituted or an unsubstituted aryl group. When $R^1$ and/or $R^2$ is a substituted aryl group, $R^1$ and/or $R^2$ has 1, 2, 3, 4 or 5 substituents $R^3$, wherein preferably, the groups $R^3$ each independently represent halogen, hydroxy, a (cyclo)alkyl, aryl, alkaryl, aralkyl, (cyclo)alkoxy, aryloxy, amido, amino, nitro, acyl, carboxyl, aryloxycarbonyl, thiol or thioether group. $R^1$ and/or $R^2$ are preferably aryl groups mono-substituted at the para position. The group $R^3$ preferably represents a hydrogen atom, a halogen atom, for instance F, Cl, Br, I, a $C_1$–$C_6$ alkoxy or cycloalkoxy group, a $C_1$–$C_6$ alkyl or cycloalkyl group, a hydroxy group, an amino group of the formula —$NR^4R^5$ where $R^4$ and $R^5$ independently of one another represent a hydrogen atom, a $C_1$–$C_6$ alkyl or cycloalkyl group or a $C_6$–$C_{12}$ aryl, aralkyl or arylalkyl group, a group of the formula —$CO_2R^6$ where $R^6$ represents a hydrogen atom (carboxyl groups), a $C_1$–$C_6$ alkyl or cycloalkyl group or a $C_6$–$C_{12}$ aryl, aralkyl or arylalkyl group (alkoxy and aryloxycarbonyl groups), a thiol group or a thioether group of the formula —$SR^7$ where $R^7$ represents a $C_1$–$C_6$ alkyl or cycloalkyl group or a $C_6$–$C_{12}$ aryl, aralkyl or arylalkyl group, a nitrile group, an acyl group of the formula —(O)$CR^8$ where $R^8$ represents a $C_1$–$C_6$ alkyl or cycloalkyl group or a $C_6$–$C_{12}$ aryl, aralkyl or alkylarylgroup, or a nitro group.

The present invention further relates to a sulphonic acid of general formula I or a salt thereof, wherein $R^1$ and $R^2$ represent a (hetero)aryl group, optionally substituted with 1 to 5 substituents $R^3$ wherein the groups $R^3$ independently of one another are as defined above, it being understood that the compounds (a)–(o), as described above, are excluded.

According to the invention formula I in particular represents the following sulphonic acids or salts thereof, preferably in enantiomerically enriched form: 1,3-diphenyl-3-oxopropane-1-sulphonic acid, 3-phenyl-1-(4-methoxyphenyl)-3-oxopropane-1-sulphonic acid, 3-phenyl-1-(4-methylphenyl)-3-oxopropane-1-sulphonic acid or 3-phenyl-1-(4-fluorophenyl)-3-oxopropane-1-sulphonic acid.

The present invention also relates to a method of preparing the (d)- or (l)-enantiomer of a sulphonic acid according to the invention or a salt thereof, a compound of general formula II:

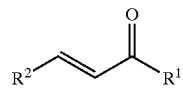

being converted with $MHSO_3$, where M may be alkali metal, an alkaline-earth metal or ammonium, to yield a compound of general formula I or a salt thereof, where $R^1$ and $R^2$ have the above meanings, and the sulphonic acid of general formula I or the salt thereof being resolved into its (d)- and (l)-enantiomers using a resolving agent. The resolving agent may comprise more than one optically active compound that can form a complex, e.g. a salt or a conjugate, with the sulphonic acid or the salt thereof.

In this description a complex is understood to mean a compound in which the resolving agent and the enantiomer are bound to each other via for instance one or more covalent bonds, ionogenic bonds, coordination bonds, hydrogen bridges and/or a combination of such bonds.

Preferably, the resolving agent comprises an organic Brønsted base, e.g. an amino functionalized compound, in particular an amine, an amino acid or a derivative thereof, for instance an ester or amide, an amino alcohol or an amino thiol. An optically active compound that is very suitable according to the invention is phenylglycine amide or p-methylphenylglycinol. This resolution in the preparation of the resolving agents involves the formation of a diastereomeric complex, in particular a complex of one enantiomer of the sulphonic acid according to the invention and the resolution agent. The invention, therefore, also relates to the diastereomeric complex of phenylglycine amide or p-methylphenylglycine and the sulphonic acid according to the invention. The conversion of such a diastereomeric complex into the enantiomers that are present in it is carried out according to known methods (for instance by treatment with acid or base followed by extraction, distillation or chromatography).

Preferably, M is an alkali metal, in particular sodium or potassium, or ammonium.

Applicant has found that the easily obtainable, anantiomerically enriched sulphonic acids according to the invention, are particularly suitable resolving agents. The present invention, therefore, further relates to the use of a (d)- or (l)-enantiomer of a sulphonic acid according to the invention or a salt thereof in the resolution of a mixture of enantiomers in a suitable solvent and to a diastereomeric complex comprising a sulphonic acid according to the invention and an enantiomerically enriched enantiomer, in particular a Brønsted base, more particularly an amino-functionalized compound e.g. an amine, an amino acid or derivative thereof, an amino alcohol or an amino thiol. It is also possible as is described in EP-A-838448 to use two or more enantiomerically enriched sulphonic acids or a salts thereof, in particular (substituted) camphor sulphonic acids or (substituted) 1-phenylalkane sulphonic acids for the resolution of racemic mixtures and mixtures already having a certain enantiomeric excess.

The present invention therefore also relates to a method of preparing a resolving agent for the resolution of a mixture of enantiomers in a suitable solvent in which a resolving agent is added to a mixture of at least two sulphonic acids according to the invention or a salt thereof, this resulting in the formation of a mixture of diastereomers of the sulphonic acids and the resolving agent, and the mixture of diastereomers subsequently being resolved into a mixture of (d)-enantiomers of the sulphonic acid or the salt thereof, or a mixture of (l)-enantiomers of the sulphonic acid or the salt thereof. So, when for instance a racemic mixture of the enantiomers of sulphonic acid A and sulphonic acid B is resolved using a resolving agent X, this racemic mixture can be resolved into a mixture containing substantially the (d)-enantiomers of sulphonic acid A and sulphonic acid B or a mixture containing substantially the (l)-enantiomers of sulphonic acid A and sulphonic acid B.

It will be clear to one skilled in the art that mixtures substantially containing either two or more (d)-enantiomers or two or more (l)-enantiomers of a sulphonic acid or salt thereof, according to the invention are eminently suitable for use as resolving agent for the resolution of racemic mixtures as described in EP-A-838448. The invention therefore also relates to the use of such a resolving agent in the resolution of a mixture of enantiomers in a suitable solvent. These enantiomers are preferably an organic Brønsted base, in particular an amino-functionalized compound, for instance an amine, an amino acid or a derivate thereof, for instance en ester or amide, an amino alcohol or an amino thiol.

The invention will be elucidated on the basis of the following examples.

EXAMPLE 1

The compounds according to general formula II were prepared according to the following general instructions (E. P.Kohler, H. N. Chadwell, Org. Synth. 2, 1).

Scheme 1

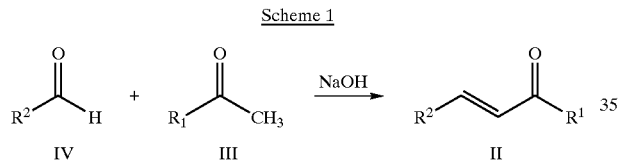

A ketone (0.43 mol) of general formula III was dissolved in 100 ml of 96% ethanol and 200 ml of water. Subsequently, 0.55 mol NaOH (21.8 g) was added.

The mixture was cooled in an ice bath and then a benzaldehyde of general formula IV (0.43 mol) was added dropwise in five minutes. The reaction mixture was stirred overnight at ambient temperature. The solid formed was then filtered off under a vacuum. When no solid had formed, the reaction mixture was extracted with ether (3 times 100 ml). The organic layers were combined, washed with brine, dried over $Na_2SO_4$ and concentrated under a vacuum. The yield generally was 90–98%.

The following compounds of general formula II were prepared:

| Compound | $R^1$ | $R^2$ |
|---|---|---|
| IIa | $C_6H_5$ | $C_6H_5$ |
| IIb | $C_6H_5$ | p-MeO-$C_6H_4$ |
| IIc | $C_6H_5$ | p-Me-$C_6H_4$ |
| IId | $C_6H_5$ | p-F-$C_6H_4$ |
| IIe | p-Br-$C_6H_4$ | $C_6H_5$ |
| IIf | p-Cl-$C_6H_4$ | $C_6H_5$ |
| IIg | p-OCH$_3$-$C_6H_4$ | $C_6H_5$ |
| IIh | p-CH$_3$-$C_6H_4$ | $C_6H_5$ |

| Compound IIa | |
|---|---|
| $^1$H-NMR (CDCl$_3$): | 7.35–7.62(m, 9H), 7.76(d, J=15.7Hz, 1H). |
| | 7.97(d, J=7.3Hz, 2H). |
| $^{13}$C-NMR (CDCl$_3$): | 119.6(d), 125.6(d), 125.9(d), |
| | 126.0(d), 126.1(d), 126.5(d), |
| | 128.1(d), 130.3(d), 132.4(s), |
| | 135.7(s), 142.3(d), 188.2(s). |

| Compound IIb | |
|---|---|
| $^1$H-NMR (CDCl$_3$): | 3.78(s, 3H), 6.87(d, J=8.8Hz, 2H), |
| | 7.34–7.56(m, 6H), 7.74(d, J=15.4Hz, 1H), |
| | 7.95(d, J=7.0Hz, 2H). |
| $^{13}$C-NMR (CDCl$_3$): | 55.2(q), 114.3(d), 119.6(d), 127.5(s), |
| | 128.3(d), 128.2(d), 130.1(d), |
| | 132.4(d), 138.4(s), 144.6(d), 190.4(s). |

| Compound IIc | |
|---|---|
| $^1$H-NMR (CDCl$_3$): | 2.35(s, 3H), 7.17(d, J=8.1Hz, 2H), |
| | 7.42–7.56(m, 6H), 7.75(d, J=15.4Hz, 1H), |
| | 7.97(d, J=7.0Hz, 2H). |
| $^{13}$C-NMR (CDCl$_3$): | 21.3(q), 121.0(d), 128.3(d), 128.5(d), |
| | 129.6(d), 132.0(d), 132.5(d), |
| | 138.2(s), 141.0(s), 144.8(d), |
| | 190.6(s). |

| Compound IId | |
|---|---|
| $^1$H-NMR (CDCl$_3$): | 7.06(m, 2H), 7.56(m, 6H), 7.73(d, 1H), |
| | 7.96(d, 2H). |
| $^{13}$C-NMR (CDCl$_3$): | 114.6(d, J=21.7Hz), 120.3(d), 127.0(d), |
| | 128.8(d), 136.6(s), 142.0(d), 160.2(s), |
| | 175.4(s), 189.2(s). |
| $^{19}$F-NMR (CDCl$_3$): | –110.2. |

| Compound IIe | |
|---|---|
| $^1$H-NMR (CDCl$_3$): | 7.0–7.4(m, 9H), 7.5–7.8(m, 2H). |
| $^{13}$C-NMR (CDCl$_3$): | 124.6(d), 130.5(s), 131.7(d), 132.2(d), |
| | 133.2(d), 134.0(d), 135.1(d), 137.8(s), |
| | 140.0(s), 148.5(d), 190.2(s). |

| Compound IIf | |
|---|---|
| $^1$H-NMR (CDCl$_3$): | 7.0–7.4(m, 9H), 7.5–7.8(m, 2H). |
| $^{13}$C-NMR (CDCl$_3$): | 124.7(d), 131.8(d), 132.1(d), 132.2(d), |
| | 133.2(d), 133.9(d), 137.8(s), 139.6(s), |
| | 148.4(d), 190.1(s). |

| Compound IIg | |
|---|---|
| $^1$H-NMR (CDCl$_3$): | 3.78(s, 3H), 6.87(d, J=8.8Hz, 2H), 7.34–7.56(m, 6H), 7.74(d, J=15.4Hz, 1H), 7.95(d, J=7.0Hz, 2H). |
| $^{13}$C-NMR (CDCl$_3$): | 55.2(q), 114.3(d), 119.6(d), 127.5(s), 128.3(d), 128.2(d), 130.1(d), 132.4(d), 138.4(s), 144.6(d), 190.4(s). |

| Compound IIh | |
|---|---|
| $^1$H-NMR (CDCl$_3$): | 2.35(s, 3H), 7.17(d, J=8.1Hz, 2H), 7.42–7.56(m, 6H), 7.75(d, J=15.8Hz, 1H), 7.97(d, 7.0 Hz, 2H). |
| $^{13}$C-NMR (CDCl$_3$): | 21.3(q), 121.0(d), 128.3(d), 128.5(d), 129.6(d), 132.0(d), 132.5(d), 138.2(s), 141.0(s), 144.8(d), 190.6(s). |

EXAMPLE 2

The compounds according to general formula I were prepared according to the following general instructions ((K. H. Pfoertner, Helv. Chim. Acta 63, 664, 1980).

An amount of 90 mmol of the compound according to the general formula II was dissolved in 150 ml of 96% ethanol. An amount of 90 mmol NaHSO$_3$ was dissolved in 100 ml of water and added to the solution of the compound according to the general formula II. The reaction mixture was heated with reflux cooling. As a rule the reaction was complete after about 3.5 hours, but continued heating with reflux cooling overnight presents no problems. The reaction mixture was subsequently cooled to ambient temperature and concentrated under a vacuum, following which the compound according to general formula I was isolated. When the compound according to general formula I precipitated during the preparation thereof, the compound was isolated by means of filtration under a vacuum. The yield generally was 95–100%.

Scheme 2

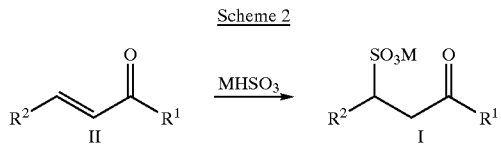

The following compounds according to general formula I were prepared, with M=N$_a$:

| Compound | R$^1$ | R$^2$ |
|---|---|---|
| Ia | C$_6$H$_5$ | C$_6$H$_5$ |
| Ib | C$_6$H$_5$ | p-MeO-C$_6$H$_4$ |
| Ic | C$_6$H$_5$ | p-Me-C$_6$H$_4$ |
| Id | C$_6$H$_5$ | p-F-C$_6$H$_4$ |
| Ie | p-Br-C$_6$H$_4$ | C$_6$H$_5$ |
| If | p-Cl-C$_6$H$_4$ | C$_6$H$_5$ |
| Ig | p-CH$_3$O-C$_6$H$_4$ | C$_6$H$_5$ |
| Ih | p-CH$_3$-C$_6$H$_4$ | C$_6$H$_5$ |

| Compound Ia | |
|---|---|
| $^1$H-NMR (DMSO-d6): | 3.61(dd, J=9.9Hz, 1H), 3.83(J=4.0 Hz, 1H), 4.20(dd, J=4.0Hz), 7.12–7.24(m, 3H), 7.35(d, J=7.0Hz, 2H), 7.50–7.91(m, 3H), 7.92(d, J=7.3Hz). |
| $^{13}$C-NMR (DMSO-d6): | 40.2(t), 60.2(d), 125.2(d), 126.3(d), 126.8(d), 127.6(d), 128.2(d), 132.0(d), 135.7(s), 137.9(s), 196.9(s). |

| Compound Ib | |
|---|---|
| $^1$H-NMR (DMSO-d6): | 3.54(dd, J=9.9Hz, 1H), 3.70(s, 3H), 3.79(dd, J=4.0Hz, 1H), 4.13(dd, J=3.7Hz, 1H), 6.76(d, J=8.8Hz, 2H), 7.24(d, J=8.8Hz, 2H), 7.48–7.89(m, 3H), 7.91(d, J=7.0Hz). |
| $^{13}$C-NMR (DMSO-d6): | 41.6(t), 55.1(q), 60.7(d), 113.1(d), 128.2(d), 129.0(d), 130.4(d), 131.4(s), 133.3(d), 137.1(s), 158.2(s), 195.6(s). |

| Compound Ic | |
|---|---|
| $^1$H-NMR (DMSO-d6): | 2.20(s, 3H), 3.53(dd, J=9.8Hz, 1H), 3.76(dd, J=4.2Hz, 1H), 4.12(dd, J=4.2Hz, 1H), 6.96(d, J=8.1Hz, 2H), 7.18(d, J=8.1Hz, 2H), 7.43–7.59(m, 3H), 7.87(d, J= 6.8 Hz, 2H). |
| $^{13}$C-NMR (DMSO-d6): | 20.8(q), 41.4(t), 61.1(d), 128.2(d), 128.3(d), 129.0(d), 129.4(d), 133.4(d), 135.5(s), 136.1(s), 137.0(s), 198.3(s). |

| Compound Id | |
|---|---|
| $^1$H-NMR (DMSO-d6): | 3.62(dd, 1H), 3.86(dd, 1H), 4.24(dd, 1H), 7.05(m, 2H), 7.37(m, 2H), 7.50(m, 2H), 7.58(m, 2H), 7.64(m, 1H), 7.92(m, 2H). |
| $^{13}$C-NMR (DMSO-d6): | 40.2(t), 59.3(d), 112.9(d, J=21.0Hz), 126.8(d), 127.5(d), 129.8(d), 132.0(d), 134.2(s), 135.6(s), 196.8(s). |
| $^{19}$F-NMR (DMSO-d6): | −118.1. |

| Compound Ie | |
|---|---|
| $^1$H-NMR (DMSO-d6): | 3.53(dd, 1H), 3.82(dd, 1H), 4.17(dd, 1H), 7.17(m, 3H), 7.33(d, 2H), 7.71(d, 2H), 7.85(d, 2H). |
| $^{13}$C-NMR (DMSO-d6): | 40.2(t), 60.2(d), 125.2(d), 126.0(s), 126.3(d), 128.1(d), 128.9(d), 130.6(d), 134.8(s), 137.9(s), 196.2(s). |

| Compound If | |
|---|---|
| $^1$H-NMR (DMSO-d6): | 3.54(dd, J=9.5Hz. 1H), 3.83(dd, 4.4Hz, 2H), 4.18(dd, J=4.4Hz, 1H), 7.14–7.24(m, 3H), 7.34(d, J=6.6Hz, 2H), 7.57(d, J=8.8Hz, 2H), 7.93(d, J=8.8Hz, 2H). |

| Compound If | |
|---|---|
| 13C-NMR (DMSO-d6): | 38.6(t), 58.6(d). 123.6(d), 124.7(d), 126.2(d), 126.6(d), 127.3(d), 132.9(s), 135.3(s), 136.3(s), 194.5(s). |

| Compound Ig | |
|---|---|
| 1H-NMR (DMSO-d6): | 3.54(dd, J=9.9Hz, 1H), 3.70(s, 3H), 3.79(dd, J=4.0Hz, 1H), 4.13(dd, J=3.7Hz, 1H), 6.76(d, J=8.8Hz, 2H), 7.24(d, J=8.8Hz, 2H), 7.48–7.89(m, 3H), 7.91(d, J=7.0Hz). |
| 13C-NMR (DMSO-d6): | 41.6(t), 55.1(q), 60.7(d), 113.1(d), 128.2(d), 129.0(d), 130.4(d), 131.4(s), 133.3(d), 137.1(s), 158.2(s), 195.6(s). |

| Compound Ih | |
|---|---|
| 1H-NMR (DMSO-d6): | 2.20(s, 3H), 3.53(dd, J=9.8Hz, 1H), 3.76(dd, J=4.2Hz, 1H), 4.12(dd, J=4.2Hz, 1H), 6.96(d, J=8.1Hz, 2H), 7.18(d, J=8.1Hz, 2H), 7.43–7.59(m, 3H), 7.87(d, J=6.8Hz, 2H). |
| 13C-NMR (DMSO-d6): | 20.8(q), 41.4(t), 61.1(d), 128.2(d), 128.3(d), 129.0(d), 129.4(d), 133.4(d), 135.5(s), 136.1(s), 137.0(s), 198.3(s). |

EXAMPLE 3

Resolution of a 1:1:1 mixture of sodium 1,3-diphenyl-3-oxo-propane-1-sulfonate (Ia), sodium 3-oxo-1-phenyl-3-(p-methoxyphenyl)propane-1-sulfonate (Ig) and sodium 3-oxo-1-phenyl-3-(p-methylphenyl)propane-1-sulfonate (Ih)

A 1:1:1 mixture of the sulphonates Ia, Ig and Ih was suspended in 20 ml 10% HCl solution. An equivalent of the resolving agent (S)-(+)-p-methylphenylglycinol was added (9.12 g) and enough isopropanol to obtain a clear solution at reflux (20 ml). The mixture was allowed to crystallize while stirring. Yield 6.4 g (23%) 1H-NMR (DMSO-d6): 2.21 (s, 3H), 2.29 (s, 3H), 3.5–3.7 (m, 5H), 4.1–4.2 (m, 3H), 5.51 (t, 1H), 6.74 (d, 1H), 6.97 (d, 1H), 7.1–7.6 (m, 13H), 7.88 (d, 2H), 8.37 (bs, 3H). The e.e. was determined via the methyl ester (obtained in a reaction with trimethylsilyl diazomethane) on chiral HPLC (AD-column). E.e. Ia: 55%; Ih: 99%; Ig: 59% The salt was recrystallized from 95/5 acetonitril/water and allowed to crystallise while stirring; yield 3.2 g (12%). The e.e. of the three sulphonates was 99% each, as determined by HPLC. The ammonium salt was obtained by addition of 12.5% NH 3 and extraction with ethyl acetate. Concentration of the water layer in vacuo gave the ammonium salt of the sulphonate mix as a white powder (3.1 g). Rotation: $[\alpha]_D$ –52.5° (c=0.22, MeOH). According to X-ray crystal structure determination of the pure diastereomeric salt the all (R)-mix is formed of Ia, Ig and Ih.

EXAMPLE 4

Resolution of sodium 3-oxo-1-phenyl-3-(p-methylphenyl)-propane-1-sulfonate (Ih)

Sodium 3-oxo-1-phenyl-3-(p-methylphenyl)-propane-1-sulfonate (Ih) (13.0 g; 40 mmol) was suspended in 40 ml 10% HCl solution. (S)-(+)-p-Methylphenylglycinol and 40 ml isopropanol was added. The mixture was heated to reflux until the mixture was clear. The mixture was allowed to crystallize while stirring. The resulting solid was removed by filtration; yield 7.9 g (43%) with an e.e. of 67%. Recrystallization from 55 ml isopropanol/water (85/15) gave 5.3 g salt (29% yield) with an e.e. of 99%. The ammonium salt was obtained by addition of 12.5% NH3 and extraction with ethyl acetate. Concentration of the water layer in vacuo gave 3.7 g of the (R)-enantiomer of the ammonium salt of the sulphonate.

EXAMPLE 5

Resolution of sodium 1,3-diphenyl-3-oxo-propane-1-sulfonate (Ia, 0.12 mol scale)

Sodium 1,3-diphenyl-3-oxo-propane-1-sulfonate (Ia) (38.5 g, 0.120 mol) was dissolved in 10% hydro-chloric acid (1.2 l) and heated to ca. 65° C. D-Phenylglycine amide (12.6 g, 0.084 mol) was added and stirring was continued until the solution was clear. The solution was allowed to cool to room temperature with stirring and the solid was collected by filtration. The solid was dried at 40° C. A second crop was obtained after cooling the filtrate to 4° C. The combined solids were recrystallized from hot water (120 ml) to give 11.0 g solid after drying (yield 20.8%, 99.7% e.e.). $[\alpha]_D$–81.8° (c=1, MeOH).

EXAMPLE 6

Resolution of sodium 1,3-diphenyl-3-oxo-propane-1-sulfonate (Ia, 1.0 mol scale)

Sodium 1,3-diphenyl-3-oxo-propane-1-sulfonate (Ia) (312.3 g, 1.0 mol) was dissolved in 10% hydrochloric acid (10 l) and heated to ca. 60° C. D-Phenylglycine amide (105 g, 0.7 mol) was added and stirring was continued until the solution was clear. The solution was allowed to cool with stirring to 15° C. over 12 h and the resulting solid was collected by filtration. The solid was dried at 40° C. (122.3 g, 27.8%, 93.1% e.e.). The solid was recrystallized from hot water (1.0 l) to give 68 g solid after drying (0.15 mol, 15%, 97% e.e.).

EXAMPLE 7

Resolution of sodium 3-oxo-1-phenyl-3-(p-methylphenyl)-propane-1-sulfonate (Ig)

A solution of sodium 3-oxo-1-phenyl-3-(p-methylphenyl) propane-1-sulfonate (Ig) (9.8 g, 0.030 mol) was dissolved in 10% hydrochloric acid (0.5 l) and heated to ca. 80° C. D-Phenylglycine amide (12.6 g, 0.084 mol) was added and stirring was continued until the solution was clear. The solution was allowed to cool to room temperature with stirring and the solid was collected by filtration (6.5 g, yield 45.5%, 15% e.e.) The solid was recrystallized from hot water (60 ml) to give 1.05 g solid after drying (yield 14.1%, 90% e.e.).

EXAMPLE 8

Resolution of sodium 3-oxo-1-phenyl-3-(p-chlorophenyl)-propane-1-sulfonate (If)

A solution of sodium 3-oxo-1-phenyl-3-(p-chlorophenyl) propane-1-sulfonate (If) (10.4 g, 0.030 mol) was dissolved 10% hydrochloric acid (300 ml) and heated to ca. 70° C. D-Phenylglycine amide (4.5 g, 0.030 mol) was added and stirring was continued until the solution was clear. The solution was allowed to cool to room temperature with stirring and the solid was collected by filtration (7.9 g, still wet, 58% e.e.) The solid was recrystallized from hot water (60 ml) to give 4.4 g solid after drying (31%, 94% e.e.). The solid was recrystallized a second time from hot water (50 ml) to give 3.8 g solid after drying (yield 27%, 98% e.e.). $[\alpha]_D$ –85.2° (c=1, MeOH).

EXAMPLE 9

Resolution of a 1:1 mixture of sodium 3-oxo-1-phenyl-3-(p-methylphenyl)propane-1-sulfonate (Ih) and sodium 3-oxo-1-phenyl-3-(p-methoxyphenyl) propane-1-sulfonate The sulfonates (10.3 g (30 mmol) Ig and 9.8 g (30 mmol) Ih) were dissolved in 240 ml 10% hydrochloric acid by heating to 60° C. D-Phenylglycine amide (6.3 g, 42 mmol) was added and stirring was continued until the solution was clear. The solution was allowed to cool with stirring to room temperature and the resulting solid was collected by filtration under suction (5.5 g, yield 20%, Ih: 90% e.e., Ig: 65% e.e., Ih:Ig=2.2:1). The solid was recrystallized from hot water (100 ml) to give 4.2 g solid after drying (15% yield, Ig: >99% e.e., Ih: 98% e.e., Ih:Ig=6.4:1). $[\alpha]_D$ –87.1° (c=1, MeOH)

EXAMPLE 10

Resolution of a 1:1 mixture of sodium 3-oxo-1-phenyl-3-(p-chlorophenyl)propane-1-sulfonate (If) and sodium 3-oxo-1-phenyl-3-(p-methoxyphenyl) propane-1-sulfonate (Ig)

The sulfonates (10.3 g (30 mmol) of Ig and 10.4 g (30 mmol) of If) were dissolved in 240 ml 10% hydrochloric acid by heating to 60° C. D-Phenylglycine amide (6.3 g, 42 mmol) was added and stirring was continued until the solution was clear. The solution was allowed to cool with stirring to room temperature and the resulting solid was collected by filtration under suction (6.6 g, yield 23%, If: 95% e.e., Ig: >95% e.e., If:Ig=7.8:1). The solid was recrystallized from hot water (100 ml) to give 5.3 g solid after drying (19% yield, If: 99% e.e., Ig: >99% e.e., If:Ig=11.2:1). $[\alpha]_D$ –87.7° (c=1, MeOH).

EXAMPLE 11

Resolution of a 1:1 mixture of sodium 3-oxo-1-phenyl-3-(p-methylphenyl)propane-1-sulfonate (Ih) and sodium 1,3-diphenyl-3-oxo-propane-1-sulfonate (Ia)

The sulfonates (9.4 g (30 mmol) of Ia and 9.8 g (30 mmol) of Ih) were dissolved in 240 ml 10% hydrochloric acid by heating to 70° C. D-Phenylglycine amide (6.3 g, 42 mmol) was added and stirring was continued until the solution was clear. The solution was allowed to cool to room temperature with stirring and the resulting solid was collected by filtration under suction (9.0 g, yield 34%, Ia: >90% e.e, Ih>90% e.e, Ia:Ih=1:1). The solid was recrystallized from hot water (50 ml) to give 7.6 g solid after drying (28% yield, Ia: >98% e.e., Ih: >98% e.e., Ih:Ia=1.6:1). $[\alpha]_D$ –83.1° (c=1, MeOH).

EXAMPLE 12

Resolution of a 1:1 mixture of sodium 3-oxo-1-phenyl-3-(p-chlorophenyl)propane-1-sulfonate (If) and sodium 1,3-diphenyl-3-oxo-propane-1-sulfonate (Ia)

The sulfonates (9.4 g (30 mmol) of Ia and 10.4 g (30 mmol) of If) were dissolved in 240 ml 10% hydrochloric acid by heating to 70° C. D-Phenylglycine amide (6.3 g, 42 mmol) was added and stirring was continued until the solution was clear. The solution was allowed to cool with stirring to room temperature and the resulting solid was collected by filtration under suction (8.3 g, yield 30%, Ia: >90% e.e, If: >90% e.e, ratio could not be determined by NMR). The solid was recrystallized from hot water (100 ml) to give 8.0 g solid after drying (29% yield, Ia: >95% e.e., If: >95% e.e., ratio could not be determined by NMR). $[\alpha]_D$ –85.9° (c=1, MeOH).

EXAMPLE 13

Resolution of sodium 1,3-diphenyl-3-oxo-propane-1-sulfonate (Ia) with L-leucine

The sulfonate (37.4 g; 120 mmol) was dissolved in 240 ml 1/1 mixture of 10% HCl/iPrOH. L-Leucine (11.0 g; 84 mmol) was added and the mixture was heated until a clear solution. The mixture was allowed to crystallize while stirring at ambient temperature. The resulting white precipitation was removed by filtration under suction and washed with iPrOH, yielding 15.4 g salt (30% yield, 85% e.e.). The salt was recrystallized from 50 ml iPrOH/H$_2$O, yielding 9.3 g salt (18% yield, 97% e.e.). $^1$H-NMR (DMSO-d6): δ0.91 (d, 6H); 1.65 (m, 2H); 1.79 (m, 1H); 3.67 (dd, 1H); 3.84 (m, 1+1H); 4.27 (dd, 1H); 7.19 (m, 3H); 7.37 (d, 2H); 7.51 (m, 2H); 7.61 (m, 1H); 7.93 (d, 2H); 8.23 (bs, 3H).

The other enantiomer of Ia is obtained after conversion into the free potassium sulfonate as compared to the D-(+)-phenylglycine amide resolutions.

EXAMPLE 14

General Procedure for Conversion into the Free Potassium Sulfonate

The salts obtained in examples 5–12 were suspended in H$_2$O. KOH (1 eq.) was added and benzaldehyde (1 eq.). The mixture was stirred overnight at room temperature; a white solid precipitates after ca. 3 hrs. This was filtered off under suction and thoroughly washed with water. The filtrate was concentrated in vacuo to obtain the resolved sulfonate as its potassium salt. The white solid was the imine of benzaldehyde and D-phenylglycine amide (D-PGA) as can be seen by NMR. No racemisation of the sulfonate was observed during this procedure.

EXAMPLE 15

Resolutions Performed with Potassium Chalconsulfonates I

General Procedure

The sulfonate or mixture of sulfonates (1 mmol) obtained in example 14 was suspended in 1,0 mL 10% HCl. The racemate was added (1 mmol) and 1 mL of iPrOH. The mixture was heated until clear. The salt was removed by filtration under suction and washed with little iPrOH. The salt was analyzed by HPLC to determine the e.e. The results are depicted in the following table. The values in parentheses are after recrystallization. Yields are calculated with respect to the racemate.

Resolution of DL-leucine
  with a (1:1:1) mixture of Ia, Ib and Ic; ee=99%; yield= 14%.

Resolution of DL-phenylglycine
  with a (1:1) mixture of Ia and If; ee=80% (94%); yield 66% with a (1:1) mixture of Ib and Id; ee=70% (96%); yield (12%)
    with a (1:1) mixture of If and Ih; ee=57%
    with Ib; ee=24%; yield=46%
Resolution of DL-p-methyl-α-methylbenzylamine
    with a (1:1:1) mixture of Ia, Ib and Ic; ee=60%; yield=30%
    with Ib; ee 22%; yield>50%
Resolution of DL-p-hydroxyphenylglycine
    with a (1:1) mixture of Ia and If; ee=49%; yield 22%.

What is claimed is:

1. A compound of formula I or a salt thereof:

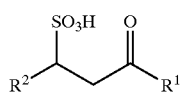

wherein each of $R^1$ and $R^2$ is a substituted or a non-substituted aryl group optionally containing one or more heteroatoms wherein said compound of formula I has an enantiomeric excess (ee) >80%.

2. A compound according to claim 1 which has an ee >90%.

3. A compound according to claim 2 which has an ee >95%.

4. A compound according to claim 1 of formula V:

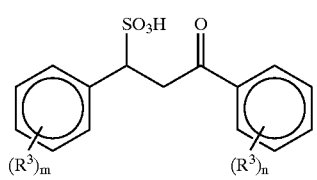

wherein, the groups $R^3$ each independently represent halogen, hydroxy, alkyl, cycloalkyl, aryl, alkaryl, aralkyl, alkoxy, cycloalkoxy, aryloxy, amido, amino, nitro, acyl, carboxyl, aryloxycarbonyl, thiol or thioether, and m and n, each independently is 0, 1, 2, 3, 4 or 5.

5. A compound according to claim 1 wherein at least one of $R^1$ and $R^2$ is a phenyl group that is substituted at the para position.

6. A compound according to claim 4 which is
1,3-diphenyl-3-oxopropane-1-sulphonic acid, 3-phenyl-1-(4-methoxyphenyl)-3-oxopropane-1-sulphonic acid,
3-phenyl-1-(4-methylphenyl)-3-oxopropane-1-sulphonic acid,
3-phenyl-1-(4-fluorophenyl)-3-oxopropane-1-sulphonic acid,
3-(4-bromophenyl)-1-phenyl-3-oxopropane sulphonic acid,
3-(4-chlorophenyl)-1-phenyl-3-oxopropane sulphonic acid.
1-phenyl-3-(4-methoxy phenyl)-3-oxopropane-sulphonic acid, or
1-phenyl-3-(4-methylphenyl)-3-oxopropane-1-sulphonic acid, or salts thereof.

7. A process for the preparation of a compound according to claim 1 which comprises adding at least one optically active amino-functionalized compound to a mixture of the (d)- and (l)-enantiomers of at least one compound of formula I or the salt thereof in a suitable solvent, whereby a diastereomeric complex is formed of the (d)- or (l)-enantiomer of the compound(s) of formula I and the optically active amino-functionalized compound, and converting the diastereomeric complex into the (d)- or (l)-enantiomer of the compound(s) of formula I or salt(s) thereof.

8. The process of claim 7 wherein the amino-functionalized compound is p-methylphenylglycinol or phenylglycine amide.

9. A process for the resolution of a mixture of enantiomers of at least one amino-functionalized compound which comprises adding at least one compound of claim 1 in a solvent to the mixture of said enantiomers, to form a diastereomeric complex of the compound of claim 1 and one of said enantiomers and
    converting the diastereomeric complex to the (d)- or (l)-enantiomer of said amino-functionalized compound.

10. A diastereomeric complex comprising a compound of claim 1 and an enantiomer of an optically active amino-functionalized compound.

11. The process of claim 7 wherein the amino functionalized compound is an amine, an amino acid or ester or amide thereof, an amino alcohol or amino thiol.

12. The process of claim 9 wherein the amino functionalized compound is an amine, an amino acid or ester or amide thereof, an amino alcohol or amino thiol.

13. The complex of claim 10 in which the amino functionalized compound is an amine, an amino acid or ester or amide thereof, an amino alcohol or amino thiol.

14. The complex of claim 13 in which the amino functionalized compound is an enantiomer of p-methylphenylglycinol or phenylglycine amide.

15. The process of claim 9 wherein the amino-functionalized compound is p-methylphenylglycinol or phenylglycine amide.

* * * * *